United States Patent [19]  
Badesha et al.

[11] Patent Number: 4,548,800  
[45] Date of Patent: Oct. 22, 1985

[54] PROCESS FOR SELENIUM PURIFICATION

[75] Inventors: Santokh S. Badesha, Ontario; Thomas W. Smith, Penfield, both of N.Y.

[73] Assignee: Xerox Corporation, Stamford, Conn.

[21] Appl. No.: 404,259

[22] Filed: Aug. 2, 1982

[51] Int. Cl.$^4$ ............................................. C01B 19/02
[52] U.S. Cl. ................................... 423/510; 423/508; 75/121
[58] Field of Search .................... 423/508, 509, 510; 549/10, 11, 332, 334, 335, 337, 338, 341, 372, 449, 511; 560/246; 75/121

[56] References Cited

U.S. PATENT DOCUMENTS

| | | | |
|---|---|---|---|
| 2,481,739 | 9/1949 | Goodman | 175/366 |
| 2,510,361 | 6/1950 | Addink | 175/366 |
| 2,860,954 | 11/1958 | Bueker et al. | 23/209 |
| 2,875,103 | 2/1959 | French | 117/200 |
| 3,723,105 | 3/1973 | Kitajima et al. | 75/134 H |
| 3,954,951 | 5/1976 | Buckley | 423/510 |
| 4,007,255 | 2/1977 | Buckley | 423/510 |
| 4,009,249 | 2/1977 | Buckley | 423/510 |
| 4,015,029 | 3/1977 | Elchisak | 427/76 |
| 4,121,981 | 10/1978 | Ward et al. | 204/38 R |
| 4,175,959 | 11/1979 | Karam et al. | 430/134 |

OTHER PUBLICATIONS

Zingaro, Ralph A. & Cooper, W. Charles, Selenium, Van Nostrand Reinhold Co., 1974, pp. 62-63.
Paul, R. C. et al., "Preparation of Dialkyl Selenites Indian", Journal of Chemistry, vol. 13, #3, Mar. 1975, pp. 292-294.
Bunton, C. A. & Hendy N. B., J. Chem. Soc. 1963 3137, "Tracer Studies in Ester Hydrolysis Part XIII."

Primary Examiner—John Doll  
Assistant Examiner—Robert L. Stoll  
Attorney, Agent, or Firm—E. O. Palazzo

[57] ABSTRACT

This invention is generally directed to an improved process for the preparation of selenium of high purity which comprises reacting selenious acid, selenium oxides, or mixtures thereof, with an alcohol, and subjecting the resulting selenium ester, subsequent to purification to a reduction reaction.

17 Claims, 1 Drawing Figure

PROCESS FOR SELENIUM PURIFICATION

BACKGROUND

This invention is generally directed to processes for the preparation of selenium, and more specifically, the present invention is directed to an improved process for preparing high purity selenium by subjecting a selenium ester to a reduction reaction. In one important embodiment of the present invention, selenium of high purity, 99.999 percent, is obtained by reacting selenious acid, selenium oxides, or mixtures thereof with an alcohol, followed by subjecting the resulting separated selenium ester to a reduction reaction. Selenium prepared from such a process can be used for a number of purposes wherein high purity materials are required, including, for example as a photoconductive imaging member in a xerographic imaging system. Additionally, the high purity selenium prepared in accordance with the process of the present invention can be alloyed with other elements, such as arsenic, tellurium, thallium, antimony, bismuth and the like, and the alloy can be incorporated into a xerographic imaging member.

The incorporation of selenium or selenium alloys into xerographic imaging members is well known in the art. These members can be subjected to a uniform electrostatic charge for the purpose of sensitizing the surface of the photoconductive layer, followed by exposure of an image to activating electromagnetic radiation such as light, which selectively dissipates the charge in the illuminated areas of the photoconductive insulating member, and wherein a latent electrostatic image is formed in the non-illuminated areas. The resulting image may then be developed and rendered visible by depositing thereon toner particles.

Recently, there has been developed layered organic and inorganic photoresponsive devices containing amorphous seleniuim, trigonal selenium, amorphous selenium alloys, halogen doped selenium, halogen doped selenium alloys, phthalocyanines, and the like. One such photoresponsive member is comprised of a substrate, a photogenerating layer containing vanadyl phthalocyanine or trigonal selenium, and a transport layer containing a diamine dispersed in a resinous binder, reference, for example, U.S. Pat. No. 4,265,990.

Selenium, or an alloy containing selenium selected for photoconductive imaging members must be of high purity, that is a purity of 99.999 percent or greater since the presence of impurities has a tendency to adversely affect the imaging properties of the photoconductive member including the electrical properties thereof, causing the copy quality obtained from such devices to be relatively poor in comparison to devices wherein selenium of a high purity is used. While processes are presently available for obtaining selenium of high purity, they involve a number of chemical and physical processing steps, and generally high temperature distillations. Accordingly, many of the prior art processes for preparing selenium and selenium alloys of high purity are complex, economically unattractive, and cause environmental contaminations. Also, such processes can be hazardous to the health of individuals in that, for example, volatile oxides are formed during the high temperature distillations, mercury must be removed in a special added step, and the chemical reagents used in the process cannot in many instances be recycled. Additionally, the prior art processes result in selenium products of different electrical properties despite adherence to the same process conditions.

One present common commercial method utilized for the preparation of high purity selenium involves the formation of selenious acid $H_2SeO_3$, from crude selenium, followed by purification, and a complicated and repeated ion-exchange process. The selenium precipitate is then further purified, melted, and subjected to distillation at relatively high temperatures, ranging from about 600 degrees Centigrade to 700 degrees Centigrade, followed by vacuum distillation. The distillation requires very complex and costly equipment, and further, any pollution products such as vaporous oxides and mercury must be safely eliminated, as indicated hereinbefore. Also, this prior art process involves a number of complex steps, and any undesirable waste materials produced must be discarded.

There is disclosed in U.S. Pat. Nos. 4,007,255 and 4,009,249 the preparation of stable red amorphous selenium containing thallium, and the preparation of red amorphous selenium. In the U.S. Pat. No. 4,007,255 there is disclosed a process for producing an amorphous red selenium material containing thallium which comprises precipitating selenious acid containing from about 10 parts per million to about 10,000 parts per million of thallium dioxide, with hydrazine, from a solution thereof in methanol or ethanol, containing not more than about 50 percent by weight of water, at a temperature between about $-20$ degrees Centigrade and the freezing point of the solution, and maintaining the resulting precipitate at a temperature of about $-13$ degrees Centigrade to about $-3$ degrees Centigrade until the solution turns to a red color. The U.S. Pat. No. 4,009,249 contains a similar disclosure with the exception that thallium is not contained in the material being treated.

In addition to the above-described methods for preparing selenium there are known a number of other processes for obtaining selenium and selenium alloys. Thus, for example, there is disclosed in U.S. Pat. No. 4,121,981 an electrochemical method for obtaining a photoreceptor comprised of a selenium tellurium layer. More specifically there is described in this patent the formation of a photogenerating layer by electrochemically co-depositing selenium and tellurium onto a substrate from a solution of their ions in such a manner that the relative amounts of selenium and tellurium which are deposited are controlled by their relative concentrations in the electrolyte, and by the choice of electrochemical conditions.

Accordingly, there is a need for improved processes for preparing selenium in high purity. Additionally, there continues to exist a need for improved simple low temperature chemical processes for preparing selenium and selenium alloys in high purity. There also continues to be a need for improved processes for obtaining selenium in high purity which processes involve a minimum number of process steps, do not require repeated ion-exchange treatments, or high temperature distillations 600–700 degrees Centigrade, and wherein most of the chemical reagents can be recycled and reused. Additionally, there continues to be a need for improved processes for preparing selenium in high yield which processes eliminate environmental hazards associated with the formation and removal of harmful materials. Also, there continues to be a need for improved processes for preparing high purity selenium that has consistent electrical properties.

OBJECTS OF THE INVENTION

It is an object of the present invention to provide processes for preparing selenium of high purity which overcome the above-noted disadvantages.

In another object of the present invention there is provided an improved process for preparing selenium of high purity by subjecting a pure selenium ester to a reduction reaction.

A further object of the present invention is the provision of an improved process for the preparation of selenium of high purity in relatively high yields.

An additional object of the present invention is the provision of a simple, low temperature process for purifying selenium, wherein most of the reactants can be recycled.

In yet another object of the present invention there are provided processes for obtaining pure selenium in high yields utilizing low temperatures, 115 degrees Centigrade or less, wherein crude selenium is treated with a strong acid, followed by the reaction of the resulting oxides with an alcohol; and thereafter subjecting the isolated ester, after purification by, for example, distillation or crystallization to a low temperature reduction reaction.

In yet another object of the present invention there is provided an improved process for obtaining high purity selenium wherein essentially no pollutants are emitted, and complex and expensive high temperature distillation apparatus, such as quartz are not needed.

It is yet another object of the present invention to provide an improved process for obtaining pure selenium with consistent, and improved electrical properties.

These and other objects of the present invention are accomplished by the provision of an improved process for the preparation of selenium of high purity which comprises reacting selenious acid, selenium oxides, or mixtures thereof, with an alcohol, followed by subjecting the resulting isolated selenium ester to a reduction reaction. In one variation of the process of the present invention, the selenious acid, selenium oxides, or mixtures thereof are obtained from the reaction of crude selenium with a strong acid, such as nitric acid, sulfuric acid or mixtures thereof. Such a process is economically attractive, particularly since few process steps are involved, high temperature distillations, and costly equipment are not required, and most of the processing materials can be recycled for use in the process.

DESCRIPTION OF FIGURE

Illustrated in FIG. 1 is a flow diagram detailing a process embodiment of the present invention.

DESCRIPTION OF THE PREFERRED EMBODIMENTS

Figure 1:
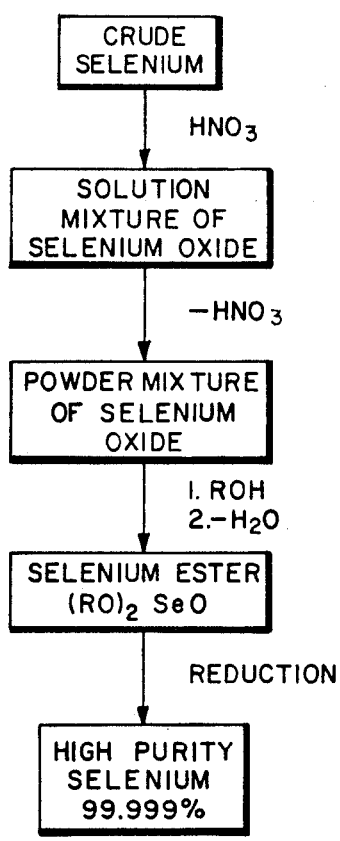

The process of the present invention will now be described with reference to the following illustrative preferred embodiments, however, process conditions, parameters, and reactants other than those specified can be selected for the process of the present invention providing the objectives thereto are achieved. Accordingly, it is not intended to be limited to the reactants and process conditions that follow.

In one important embodiment of the present invention, there is provided an improved process for the preparation of selenium in a purity of 99.999 percent, wherein selenious acid is reacted with an aliphatic alcohol, thereby resulting in the formation of a liquid dialkyl selenite ester, of the formula $(RO)_2SeO$, wherein R is an alkyl group as defined herein. This selenite ester subsequent to separation from the reaction mixture is further purified by distillation and then subjected to a reduction reaction wherein selenium of high purity, and in high yield is obtained. In a variation of the process of the present invention, the selenious acid, selenium oxides, and mixtures thereof are obtained by dissolving crude selenium, in strong acids such as nitric acid, sulfuric acid, and mixtures thereof.

The aliphatic alcohol selected for the process of the present invention is generally of the formula ROH, wherein R is an alkyl group containing from 1 to about 30 carbon atoms, and preferably from 1 to about 6 carbon atoms. Illustrative examples of preferred R groupings for the aliphatic alcohol, and the selenite ester include methyl, ethyl, propyl, butyl, pentyl, and hexyl, with methyl and ethyl being preferred. Specific preferred alcohols selected for the process of the present invention include methanol, ethanol and propanol.

In another important variation of the process of the present invention there can be selected for formation of the ester a diol instead of an aliphatic alcohol. The diol selected is generally of the formula $HO(CR_1R_2)_nOH$ wherein $R_1$ and $R_2$ are hydrogen, or alkyl groups as defined herein, and n is a number ranging from 1 to about 10. Examples of preferred diols that may be selected include ethylene glycol, and propylene glycol.

The selenium esters resulting from the diol reaction are of the general formula:

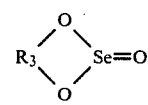

wherein $R_3$ is an alkylene group such as ethylene, methylene, propylene, and the like.

In one illustrated process embodiment of the present invention, a crude selenium material available from Fisher Scientific Company, is oxidized to its corresponding oxides by dissolving this material in a strong acid, such as nitric acid. As strong acids, there is selected for the process of the present invention commercially available concentrated nitric acid, commercially available concentrated sulfuric acid, and mixtures thereof. When mixtures of acids are utilized generally from about 20 percent of sulfuric acid and about 80 percent of nitric acid are employed however percentage mixtures can range from between about 5 percent sulfuric acid to about 95 percent nitric acid, and preferably from about 10 percent sulfuric acid to about 90 percent nitric acid. The preferred acid is nitric acid, primarily since it is a stronger oxidizing acid for selenium. Other chemical reagents such as hydrogen peroxide, molecular oxygen, and the like, can also be used to effect this conversion. Generally the crude material is about 98 percent pure, and contains a number of impurities, such as arsenic, bismuth, cadmium, chromium, iron, sodium, magnesium, lead, antimony, tin, silicon, titanium, nickel, lead, thallium, boron, barium, mercury, zinc, other metallic and non-metallic impurities, and the like.

The amount of crude selenium to be dissolved can vary depending for example, on the amount of high purity product desired. Normally from about 1 pound to about 1.5 pounds of crude selenium are dissolved, and preferably from about 1 pound to about 500 grams are dissolved, however it is to be appreciated that substantially any amount of crude selenium can be dissolved if desired.

Generally, the acid used for dissolving the crude selenium product is added thereto in an amount of from about 600 milliliters to about 1,200 milliliters, for each pound of selenium being dissolved, and preferably from about 800 milliliters to about 900 milliliters.

The resulting suspension of selenium and acid are stirred at a sufficient temperature so as to cause complete dissolution of the crude selenium. In one specific embodiment, the suspension is continuously stirred at a temperature of between about 65 degrees Centigrade to about 85 degrees Centigrade for a sufficient period of time to cause complete dissolution of the crude selenium, as noted by the formation of a clear solution. This solution is usually formed in about 1 hour to about 3 hours, however the time can vary significantly depending on the process parameters selected. Thus, for example, very extensive stirring at higher temperatures will result in complete dissolving of the crude selenium in about an hour or less, while low temperatures, less than 30 degrees Centigrade, and slow stirring will not cause the crude selenium to be dissolved until about 3 hours or longer.

Thereafter, the concentrated acid mixture is separated from the resulting clear solution by a number of known methods including distillation at the appropriate temperature, for example 110 degrees Centigrade when nitric acid is being separated. The resulting separated acid can be collected in a suitable container, such as distillation receiver, and subsequently recycled and repeatedly used for dissolving the crude selenium product.

Subsequent to the distillation reaction, and separation of the acid from the solution mixture, there results a white powder, identified as selenious acid $H_2SeO_3$, and other oxides of selenium, such as selenium dioxide. To this powder there is then added an aliphatic alcohol of the formula ROH, wherein R is an alkyl group containing from 1 to about 30 carbon atoms, and preferably from about 1 to about 6 carbon atoms or a diol, causing the formation of a liquid selenium ester. Generally from about 500 milliliters to about 800 milliliters, and preferably from about 600 milliliters to about 700 milliliters of aliphatic alcohol, or diol, are utilized for conversion to the selenium ester, however, other appropriate amounts of alcohol can be selected.

Water formed subsequent to the addition of the aliphatic alcohol or diol, can be removed if desired by an azeotropic distillation process. This is accomplished by boiling the mixture with various azeotropic substances, such as aliphatic and aromatic hydrocarbons including toluene, benzene and pentane. The known azeotropic distillation processes can be effected at temperatures at which the azeotropic agent begins to boil, thus when pentane is used this temperature ranges from about 30 degrees Centigrade to about 35 degrees Centigrade. While it is not necessary to azetropically remove water from the reaction mixture, since the purity of the resulting selenium product will not be adversely affected, it is preferred in the process of the present invention to cause this removal in order, for example, that higher yields of product might be obtained.

The complete removal of water and thus total conversion to the selenium ester is generally accomplished in a period of from about 8 to about 10 hours.

The excess aliphatic alcohol and hydrocarbons, if any, selected for the azeotropic distillation, are then removed by subjecting the resulting reaction mixture to distillation, generally under a vacuum of about 5 millimeters of mercury, and at a temperature of from about 70 degrees Centigrade to about 80 degrees Centigrade. There is then collected, when ethanol is utilized, the pure colorless liquid selenium ester diethyl selenite $(C_2H_5)_2SeO$, as identified by spectroscopic analysis, however, other dialkyl selenite esters can also be obtained with different alcohols.

The pure, isolated dialkyl selenite ester can then be directly reduced to pure selenium by a reduction reaction, or as an optional step prior to reduction, the pure ester can be dissolved in water or an organic solvent, such as cellosolve, ethanol, and the like, resulting in a solution containing from about 25 percent to about 60 percent, and preferably from about 40 percent to about 50 percent, of the pure selenium ester.

The reduction reaction can be accomplished at various suitable temperatures, dependent on, for example, the reducing agent selected, and the solvent system used. Generally, the reduction reaction is accomplished at relatively low temperatures not exceeding about 100 degrees Centigrade. Specifically, the reduction reaction temperature can range from about 25 degrees Centigrade to about 100 degrees Centigrade, depending for example on the reducing agent being employed. Illustrative examples of reducing agents include those well known in the art such as hydrazine, sulfur dioxide, hydroxylamine, hydroquinones, thioureas, glyoxal, ascorbic acid, pyrroles, phosphates, phosphites, and the like. The preferred reducing agents are hydrazine and sulfur dioxide.

The amount of reducing agent needed is dependent on a number of factors, such as its chemical composition, the manner in which it is used, reaction temperatures, concentrations of reactants employed, and the like. The hydrazine is usually added in an equimolar quantity until completion of the reduction reaction, while the sulfur dioxide is generally bubbled through the solution of dialkyl selenite ester in water for a period of time sufficient to cause complete precipitation of the selenium. Generally, this bubbling is continued for a period of about 1 hour to about 5 hours, and preferably from about 2 hours to about 3 hours, although times outside these ranges can be selected, providing the objectives of the present invention are achieved.

Upon completion of the reduction reaction there results a selenium precipitate of a certain color, the specific color produced being dependent on, for example, the reducing agent selected, and the reaction temperature. Thus when hydrazine is the reducing agent, a black precipitate of crystalline selenium results, while when sulfur dioxide is selected as the reducing agent a red precipitate of amorphous selenium is produced. The desired high purity selenium can then be separated from the reaction mixture by a number of suitable known methods including filtration. Subsequently, as an optional treatment step, the separated selenium can be washed with suitable solvents such as water and cellosolve, followed by allowing the selenium to dry in air. Normally about 500 milliliters or more of washing solvent is selected for each pound of precipitated selenium.

The purity of the selenium obtained in accordance with the process of the present invention was determined by Emission Spectroscopy, while the identity and purity of the selenium ester was determined by infrared, (NMR), ultraviolet (UV), mass spectral analysis, and elemental analysis for carbon, oxygen and hydrogen. Results obtained with the process of the present invention, wherein purity is determined by Emission Spectroscopy are illustrated in Table I that follows:

TABLE I

| ELEMENTS | A | B | C | D | E |
|---|---|---|---|---|---|
| Ag | 1* (ppm) | — | — | — | — |
| Al | 5+ | 1 | — | 2 | 2 |
| As | m* | — | — | — | — |
| B | — | — | — | — | — |
| Ba | — | — | — | — | — |
| Bi | m | — | — | — | — |
| Ca | 10+ | 3 | 1 | 1 | −1 |
| Cd | 20+ | — | — | — | — |
| Co | — | — | — | — | — |
| Cr | 10+ | — | — | — | — |
| Cu | 2 | 0.2 | — | 0.2 | 2 |
| Fe | m | 2 | 1 | 2 | 2 |
| Hg | 10 | — | — | — | — |
| Na | 20 | — | — | — | — |
| Mg | 20 | 10 | 5 | 3 | 5 |
| Mn | 10 | — | — | — | — |
| Mo | 15 | — | — | — | — |
| Ni | 10+ | — | — | — | — |
| Pb | m | — | — | — | — |
| Sb | 20+ | — | — | — | — |
| Sn | 20+ | — | — | — | — |
| Si | 20+ | 10 | 5 | 7 | 5 |
| Te | 10+ | — | — | — | — |
| Ti | 20+ | — | — | — | — |
| Tl | — | — | — | — | — |
| Zn | 5+ | — | — | — | — |
| Se | Balance | Balance | Balance | Balance | Balance |

*The values reported are in parts per million, with m representing the presence of the impurity, above 500 parts per million (ppm) indicated. The (—) indicates that no detection of the element specified was determined by Emission Spectroscopy. Balance signifies that the remaining part of the composition contained selenium in parts per million. Moreover, it is believed that the silicon (Si), magnesium, (Mg), and calcium, (Ca), impurities result primarily from the glassware and fritted funnels selected for the process described.

The letter designations A, B, C, D, and E, signify that the following selenium sources were selected for treatment.

A—commercial crude selenium
B—reclaimed selenium (hydrazine reduced)
C—reclaimed selenium (sulfur dioxide reduced)
D—commercial grade selenium dioxide (hydrazine reduced)
E—commercial grade selenious acid (hydrazine reduced)

Additionally, when selecting hydrazine as the reducing agent, trigonal selenium is generally obtained rather than the amorphous, such trigonal selenium being of a 99.999 percent purity.

In accordance with the process of the present invention, the selenium product is also obtained in high yields, that is yields ranging from about 85 to 95 percent, and usually from about 90 to 95 percent. Accordingly, not only is the selenium product obtained in exceptional purity, namely 99.999 percent rendering it highly useful as an electrostatic imaging member in xerographic imaging systems, but such a product is obtained in high yields, rendering the process of the present invention economically attractive, and very feasible.

The high purity selenium prepared in accordance with the process of the present invention can be utilized as an imaging member in a xerographic imaging system. Such a member is generally designated as an inorganic photoresponsive device, or a layered organic photoresponsive device. As an inorganic photoresponsive device the prepared selenium is deposited on an aluminum substrate and the resulting member is subjected to a uniform electrostatic charge, followed by exposing the resulting sensitized surface to an image pattern by electromagnetic radiation such as light. The light impingement on the device results in a selective dissipation of the initially applied charge, resulting in a positive electrostatic image, which is then developed in accordance with known methods by applying oppositely charged toner particles to the member. The resulting developed image can then be transferred to a suitable substrate such as paper, and permanently affixed thereto.

Examples of layered organic photoresponsive devices containing the high purity selenium prepared in accordance with the process of the present invention include those devices comprised of generating and transport layers as described in U.S. Pat. No. 4,265,990, the disclosure of which is totally incorporated herein by reference. As examples of generating layers for such devices there is selected trigonal selenium, while examples of the transport layer disclosed in this patent include various diamines dispersed in an active resinous binder mixture.

The following examples illustrate preferred embodiments of the present invention which examples are not intended to limit the scope of the present invention, it being noted that various alternative parameters which are not specifically mentioned are included within the scope of the present invention. Parts and percentages are by weight unless otherwise indicated. The selenium source material selected includes crude selenium, commercial grade selenious acid and selenium dioxide. The purity of the reclaimed selenium was determined by Emission Spectroscopy.

EXAMPLE I

This example describes the preparation of diethyl selenide from a crude selenium source material, by first converting the crude selenium to selenious acid by treatment with nitric acid, followed by a condensation reaction with an alcohol wherein there results a dialkyl selenite as identified by infrared, nuclear magnetic resonance (NMR), mass spectroscopy, and elemental analysis for hydrogen, oxygen, and carbon.

One pound of crude selenium powder was dissolved in 1 liter of concentrated nitric acid by stirring and warming over a period of 3 hours in a 2-liter round bottom (RB) flask. After a clear solution was obtained, nitric acid was distilled off at a temperature of 110–112 degrees Centigrade, and and remaining traces of nitric acid were then removed under high vacuum. The resulting white residue was dissolved in 700 milliliters of absolute ethanol, and any water formed was removed azeotropically with 600 milliliters of benzene. The azeotropic distillation was completed in about 15 hours. There was then removed by vacuum distillation at normal pressure benzene and excess ethanol, and the resulting residue was fractionally distilled under high vacuum. Pure diethyl selenite which boils at 65 degrees Centigrade/3 mm was collected. The grey residue left in the flask was dissolved in absolute ethanol (800 ml) and benzene (600 ml). Any water formed was removed azeotropically and an additional crop of diethyl selenite was obtained. The total yield of diethyl selenite was 90 percent, (956 grams). This yield can be increased further by recycling the grey residue remaining in the flask.

EXAMPLE II

This example describes the reduction of the pure diethyl selenite prepared in accordance with Example I with sulfur dioxide in an aqueous media.

Sulfur dioxide gas was slowly bubbled for two hours at room temperature through a solution of 400 grams of the diethyl selenite prepared in accordance with Example I in 1,000 milliliters of deionized water contained in a 2 liter Erlenmeyer flask. A red precipitate of amorphous selenium began separating out of the solution. The resulting red precipitate was then collected by filtration, washed several times with water until the washings are neutral (pH=7). The precipitate was then vacuum dried and weighed. A total yield of 110 grams (65 percent) of red amorphous selenium was obtained. This yield can be improved by increasing the reaction temperature and by bubbling sulfur dioxide for a period of time sufficient to cause disappearance of the red color in the filtrate.

Emission spectral analysis indicated that the resulting selenium had only the following contaminations: Fe, 1 ppm; Mg, 5 ppm; and Si, 5 ppm, and that the selenium obtained had a purity of 99.999 percent.

EXAMPLE III

This example describes the reduction of the diethyl selenite prepared in accordance with the process of Example I, with hydrazine in an organic media.

A solution of diethyl selenite (400 grams) in cellosolve (500 ml) was charged to a 3 liter 3-necked round bottom (RB) flask equipped with a reflux condenser, graduated addition funnel and Teflon ® paddle stirrer. A solution of 85 grams of hydrazine in 100 milliliters of cellosolve was added dropwise through the addition funnel to the stirring solution of the selenite. This addition consumed approximately 1 hour. The resulting black precipitate was collected by filtration with a sintered glass filter, washed with 200 milliliters (4×50 ml) of cellosolve, dried and weighed.

There resulted 169 grams (99 percent yield) of selenium. Emission spectral analysis indicated that the resulting selenium had only the following contaminations: Al, 1 ppm; Ca, 3 ppm; Cu, 0.2 ppm; Fe, 2 ppm; Mg; 10 ppm; and Si, 10 ppm; and further that the selenium obtained had a purity of 99.999 percent.

EXAMPLE IV

This example describes the conversion of commercial grade selenious acid (94 percent) into diethyl selenite.

A mixture of selenious acid (100 grams), absolute ethanol (200 ml) and benzene (200 ml) was charged to a 1 liter RB flask equipped with a Dean-Stark refluxing column. This mixture was stirred at room temperature under an atmosphere of argon until a clear solution was obtained. The reaction mixture was then slowly refluxed and the water removed azeotropically. About 7 hours were required to complete the reaction to this point. Excess ethanol and benzene are removed by distillation, and the resulting grey residue was distilled under reduced pressure. There were collected 89 grams of a colorless liquid distilling at 68 degrees Centigrade/5 mm. The grey solid residue was again dissolved in a mixture of ethanol (100 ml) and benzene (150 ml). The water was removed azeotropically, and after removing excess ethanol and benzene the residue was fractionally distilled. The fraction distilling at 68 degrees Centigrade/5 mm was collected, and identified as pure diethyl selenite, by infrared, nuclear magnetic resonance (NMR), and confirmed by elemental analysis for carbon, oxygen, and hydrogen. The amount of this fraction was 33 grams, thereby increasing the overall yield of diethyl selenite to 122 grams (91 percent).

EXAMPLE V

This example describes the reduction of diethyl selenite obtained, from commercial grade selenious acid, with hydrazine in an organic media.

A solution of 122 grams of the diethyl selenite ester prepared in accordance with Example IV, in 500 milliliters of cellosolve was reduced with a solution of 15 milliliters of hydrazine in 50 milliliters of cellosolve as described in Example III, and 51.5 grams (99.999 percent) of high purity selenium was obtained. Emission spectral analysis indicated that the resulting selenium had only the following contaminations: Al, 2 ppm; Ca, 1 ppm; Cu, 0.2 ppm; Fe, 2 ppm; Mg; 3 ppm; and Si, 7 ppm; and further that the selenium obtained was of a purity of 99.999 percent.

EXAMPLE VI

This example describes the conversion of selenium dioxide into dimethyl selenite.

A mixture of selenium dioxide (50 grams), p-toluene sulfonic acid (5 grams) in 500 milliliters of methanol was charged to a 1 liter RB flask fitted with a Dean-Stark apparatus. The reaction mixture was refluxed and stirred on a magnetic stirrer for 5 hours during which time a clear solution results. Chloroform (200 ml) was then added to the reaction flask and water removed azeotropically. Excess methanol and chloroform were removed by distillation, and the residue in the flask was then distilled under high vacuum. Pure dimethyl selenite, as identified by infrared, nuclear magnetic resonance (NMR), mass spectroscopy, and elemental analysis for carbon, hydrogen, and oxygen, and which distills at 43 degrees Centigrade/5 mm of mercury was collected. A total yield of 60 grams (85 percent) of this ester was collected.

EXAMPLE VII

A solution of 156 grams of dimethyl selenite, prepared in accordance with Example VI, in 500 ml of cellosolve was charged to a 1 liter Erlenmeyer flask. The mixture was stirred at room temperature for 2 minutes on a magnetic stirrer. A solution of 20 milliliters of hydrazine in 50 milliliters of cellosolve was then added dropwise to the above stirring reaction mixture. The addition consumed approximately 1 hour. The reaction was exothermic and $N_2$ gas was evolved. The resulting black precipitate was collected by filtration, washed and dried as described in Example III. A total of 75 grams (95 percent) of crystalline selenium was collected. Emission spectral analysis indicated that the resulting selenium had only the following contaminations: Al, 2 ppm; Ca, 1 ppm; Cu, 0.2 ppm; Fe, 2 ppm; Mg; 3 ppm; and Si, 7 ppm; and further that the selenium obtained had a purity of 99.999 percent.

EXAMPLE VIII

The high purity selenium product prepared in accordance with the process of Examples I–VII were then formulated into a xerographic imaging member by vacuum depositing this material on an aluminum substrate. The aluminum substrate had a thickness of about 2,000 to about 3,000 microns, and the selenium is deposited thereon in a thickness of about 50 to about 60 microns.

These imaging devices are then incorporated as a photoconductive imaging member in a xerographic imaging system, and subsequent to development, there resulted high quality images of excellent resolution.

There is illustrated in FIG. 1, a flow diagram for an embodiment of the process of the present invention, wherein crude selenium is treated with nitric acid resulting in the formation of a solution of a mixture of selenium oxides. Any excess nitric acid is then removed by distillation and there results a powdered mixture of selenium oxides. To this powdered mixture is added an alcohol, ROH, followed by the azeotropic removal of water. Subsequent to distillation there results a pure selenium ester. This selenium ester is then subjected to a reduction reaction, with hydrazine or sulfur dioxide, for example, resulting in a high purity selenium product, 99.999 percent as determined by Emission Spectroscopy. Alternatively, the pure selenium ester can be obtained from the reaction of crude selenium dioxide, commercially available, or the acid of selenium, $H_2SeO_3$, also commercially available, with an alcohol, ROH, followed by the azeotropic removal of water. Identification, and purity of the selenium ester was determined by infrared analysis, nuclear magnetic resonance (NMR), mass spectroscopy, ultraviolet, and elemental analysis for carbon, hydrogen, and oxygen.

Other modifications of the present invention will occur to those skilled in the art based upon a reading of the disclosure of the present application and these modifications are intended to be included within the scope of the present invention.

We claim:

1. A process for the preparation of selenium of high purity which comprises reacting selenious acid, selenium oxides, or mixtures thereof, with an alcohol, and subjecting the resulting selenium ester, subsequent to purification to a reduction reaction.

2. A process in accordance with claim 1 wherein the alcohol is of the formula ROH, wherein R is an alkyl group containing from 1 carbon atom to about 6 carbon atoms.

3. A process in accordance with claim 2 wherein the alcohol is methanol or ethanol.

4. A process in accordance with claim 1 wherein the selenious acid, selenium oxides, or mixtures thereof result from the reaction of crude selenium with a strong acid.

5. A process in accordance with claim 4 wherein the acid is nitric acid.

6. A process in accordance with claim 1 wherein the resulting selenium ester is of the formula $(RO)_2SeO$, wherein R is an alkyl group containing from 1 carbon atom to about 6 carbon atoms.

7. A process in accordance with claim 6 wherein R is methyl or ethyl.

8. A process in accordance with claim 1 wherein the reducing agent is selected from hydrazine, sulfur dioxide, thiourea, hydroxylamine, hydrochloride, or hydrazine hydrochloride.

9. A process in accordance with claim 1 wherein selenium is obtained in a purity of 99.999 percent.

10. A process in accordance with claim 1 wherein the resulting ester is purified by distillation, or crystallization.

11. A process in accordance with claim 1 wherein the reduction reaction is accomplished at a temperature of from about 25° C. to about 80° C.

12. A process for the preparation of selenium of high purity which comprises reacting selenious acid, selenium oxides, or mixtures thereof, with a diol of the formula $HO(CR_1R_2)_nOH$ wherein $R_1$ and $R_2$ are alkyl groups containing from 1 to about 30 carbon atoms, and n is a number of from about 1 to about 10, and subjecting the resulting isolated selenium ester, subsequent to purification to a reduction reaction.

13. A process in accordance with claim 12 wherein the resulting selenium ester is of the formula

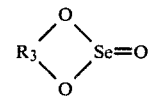

wherein $R_3$ is an alkylene group.

14. A process in accordance with claim 12 wherein the diol is ethylene glycol, or propylene glycol.

15. A process for the preparation of selenium of a purity of 99.999% which comprises reacting a selenium oxide with ethanol, separating from the reaction mixture the ester of selenium resulting, purifying the selenium ester by crystallization or distillation, and subsequently subjecting the isolated pure selenium ester to a reduction reaction with hydrazine or sulfur dioxide, wherein the reaction with ethanol is accomplished at a temperature of from about 65° C. to about 85° C., and the reduction reaction is accomplished at a temperature of from about 25° C. to about 100° C.

16. A process for the preparation of selenium of a purity of 99.999% which comprises reacting crude selenium powder with nitric acid, subjecting the resulting selenium oxide to a reaction with ethanol, removing water from the reaction mixture, separating the resulting diethyl selenite ester, purifying the diethyl selenite ester by crystallization or distillation, followed by subjecting the separated pure ester to a reduction reaction with hydrazine or sulfur dioxide, wherein the nitric acid reaction is accomplished at a temperature of from about 65° C. to about 85° C., and the reduction reaction is accomplished at a temperature of from about 25° C. to about 100° C.

17. A process in accordance with claim 16 wherein water is removed from the reaction mixture by an azeotropic distillation process.

* * * * *